United States Patent [19]

Haag et al.

[11] 4,409,412

[45] Oct. 11, 1983

[54] PROCESS FOR PRODUCING ALKYL AROMATIC COMPOUNDS

[75] Inventors: Werner O. Haag; Tracy J. Huang, both of Lawrenceville, N.J.

[73] Assignee: Mobil Oil Corporation, New York, N.Y.

[21] Appl. No.: 423,337

[22] Filed: Sep. 24, 1982

Related U.S. Application Data

[62] Division of Ser. No. 230,176, Jan. 30, 1981.

[51] Int. Cl.$^3$ ............................................. C07C 2/86
[52] U.S. Cl. ................................. 585/454; 585/468
[58] Field of Search ........................... 585/454, 468

[56] References Cited

U.S. PATENT DOCUMENTS

| | | | |
|---|---|---|---|
| 4,049,738 | 9/1977 | Young | 585/454 |
| 4,086,289 | 4/1978 | Seitzer | 585/454 |
| 4,152,364 | 5/1979 | Chu | 585/454 |
| 4,157,338 | 6/1979 | Haag et al. | 260/449 M |
| 4,159,995 | 7/1979 | Haag et al. | 585/322 |
| 4,279,830 | 7/1981 | Haag et al. | 585/322 |

*Primary Examiner*—Curtis R. Davis
*Attorney, Agent, or Firm*—Michael G. Gilman; Charles J. Speciale

[57] ABSTRACT

A process for alkylating aromatic compounds wherein the product aromatics are provided with one or more alkyl groups possessing at least two carbon atoms is disclosed wherein starting aromatic compound(s) and an alkylating atent which is a mixture of hydrogen and/or a hydrogen-containing substance which provides hydrogen under process conditions and a carbon oxide, e.g., a mixture of syngas (hydrogen and carbon monoxide) are reacted at elevated temperature in the presence of an activated catalyst containing metal values selected from the group consisting of iron, cobalt, ruthenium, manganese, rhodium and osmium, and a zeolite having a constraint index of 12 or less, e.g., ZSM-5. The alkylated aromatics can be dealkylated by known and conventional means to provide olefin and the dealkylated aromatics can be recycled to the alkylation zone.

6 Claims, No Drawings

PROCESS FOR PRODUCING ALKYL AROMATIC COMPOUNDS

This is a division of copending application Ser. No. 230,176, filed Jan. 30, 1981.

BACKGROUND OF THE INVENTION

1. Field of the Invention

This invention relates to the field of aromatic compound synthesis and, more particularly, to the preparation of alkyl aromatic compounds and catalyst compositions useful therefor.

2. Description of the Prior Art

Alkylation of aromatic hydrocarbons utilizing crystalline aluminosilicate catalysts has heretofore been described. U.S. Pat. No. 3,251,897 to Wise describes alkylation of aromatic hydrocarbons in the presence of X- or Y-type crystalline aluminosilicate zeolites, specifically such type zeolites wherein the cation is rare earth and/or hydrogen. U.S. Pat. No. 3,751,504 to Keown, et al. and U.S. Pat. No. 3,751,506 to Barress describe vapor phase alkylation of aromatic hydrocarbons with olefins, e.g., benzene with ethylene, in the presence of a ZSM-5 type zeolite catalyst.

Processes for the catalytic methylation of aromatic hydrocarbons, e.g., toluene to provide a mixture of xylene isomers, employing hydrogen and carbon monoxide as the methylating agent are described in U.S. Pat. Nos. 3,718,704 to Chapman, et al. and 4,086,289 to Seitzer. Due to the nature of the catalysts, in the case of Chapman, a mixture of certain metal oxides such as zinc oxide and chromia (zinc chromite) and in the case of Seitzer, zinc chromite mixed with an alkali metal exchanged molecular sieve containing an excess of alkali metal carbonate, these processes are incapable of incorporating alkyl groups other than methyl into the aromatic ring.

SUMMARY OF THE INVENTION

It has now been discovered that one or more alkyl side chains possessing at least two carbon atoms can be incorporated into an aromatic compound by reacting the aromatic compound with an alkylating agent which is a gaseous mixture of hydrogen and/or a hydrogen-containing substance which provides hydrogen under process conditions and a carbon oxide, in the presence of a catalytically effective amount of a heterogenous catalyst comprising a metal or metal-containing component selected from the group consisting of iron, cobalt, ruthenium, manganese, rhodium and osmium and a zeolite which possesses a constraint index as hereinafter defined of 12 or less.

In addition to providing an economical one-step synthesis for the industrially important $C_{2+}$ alkyl aromatics, the alkylation process herein also offers a practical and efficient route to the production of olefins which are obtained herein by dealkylation of the product alkyl aromatics employing known and conventional methods. The dealkylated aromatics may then be recycled to the alkylation reaction for conversion to further quantities of alkyl aromatics. These reactions, alkylation and dealkylation, can be illustrated for the preferred alkylating agent herein, i.e., synthesis gas or "syngas" which is a gaseous mixture containing hydrogen and carbon monoxide obtained from the gasification of carbonaceous materials such as coal or natural gas, as follows (Ar is aryl and n=2 to about 22):

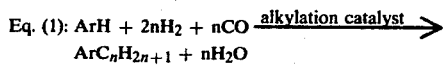

Eq. (1): $ArH + 2nH_2 + nCO \xrightarrow{\text{alkylation catalyst}}$
$ArC_nH_{2n+1} + nH_2O$

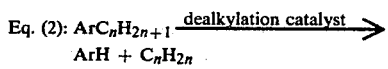

Eq. (2): $ArC_nH_{2n+1} \xrightarrow{\text{dealkylation catalyst}}$
$ArH + C_nH_{2n}$ or

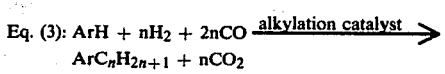

Eq. (3): $ArH + nH_2 + 2nCO \xrightarrow{\text{alkylation catalyst}}$
$ArC_nH_{2n+1} + nCO_2$ and

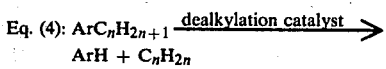

Eq. (4): $ArC_nH_{2n+1} \xrightarrow{\text{dealkylation catalyst}}$
$ArH + C_nH_{2n}$ With recycle of the dealkylated aromatic compound, it is seen from the above that the net reaction providing olefin only consumes syngas as indicated by the equation:

$$2nH_2 + nCO \rightarrow C_nH_{2n} + nH_2O \qquad \text{Eq. (5)}$$

or

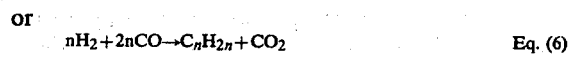

$$nH_2 + 2nCO \rightarrow C_nH_{2n} + CO_2 \qquad \text{Eq. (6)}$$

While it is known that syngas can be converted directly to light olefins in relatively high yield employing a variety of catalyst compositions, such syntheses have been impractical or uneconomical due to problems associated with inadequate catalyst stability. The catalysts employed in the alkylation process of the present invention not only possess high levels of activity, but they also possess a degree of stability which far exceeds that of catalysts heretofore used in the direct conversion of syngas to light olefins.

DESCRIPTION OF THE PREFERRED EMBODIMENTS

The term "aromatic" in reference to the alkylatable compounds which are useful herein is to be understood in accordance with its art-recognized scope which includes substituted and unsubstituted mono- and polynuclear compounds. Compounds of an aromatic character which possess a hetero atom are also useful provided they do not act as catalyst poisons. Thus, for example, thiophene can be alkylated in accordance with the process of this invention but pyridine which is basic in character would ordinarily not be considered a useful starting material herein due to its adverse effect on the instant catalysts all of which are acidic in nature.

Substituted aromatic compounds which can be alkylated herein must possess at least one hydrogen atom directly bonded to the aromatic nucleus. The aromatic rings can be substituted with one or more alkyl, aryl, alkaryl, hydroxy, alkoxy, aryloxy, cycloalkyl, halide, and/or other groups which do not interfere with the alkylation reaction.

Suitable aromatic hydrocarbons include benzene which is preferred, especially where the sole function of the aromatic is to serve as a temporary trapping device for alkyl groups in an overall synthesis for light olefins as described above, naphthalene, anthracene, naphthacene, chrysene, pyrene, triphenylene, pentacene, picene, perylene, coronene and phenanthrene.

Generally the alkyl groups which can be present as substituents on the aromatic compound contain from one to 22 carbon atoms and preferably from about one to eight carbon atoms, and most preferably from about one to four carbon atoms.

Suitable alkyl substituted aromatic compounds include toluene, xylene, isopropylbenzene, normal propylbenzene, alpha-methylnaphthalene, ethylbenzene, cumene, mesitylene, durene, p-cymene, butylbenzene, pseudocumene, o-diothylbenzene, m-diethylbenzene, p-diethylbenzene, isoamylbenzene, isohexylbenzene, pentaethylbenzene, pentamethylbenzene; 1,2,3,4-tetraethyl-benzene; 1,2,3,5-tetramethylbenzene; 1,2,4-triethylbenzene; 1,2,3-trimethylbenzene, m-butyltoluene; p-butyltoluene; 3,5-diethyltoluene; o-ethyltoluene; p-ethyltoluene; m-propyltoluene; 4-ethyl-m-xylene; dimethylnaphthalenes; ethylnaphthalene; 2,3-dimethylanthracene; 9-ethylanthracene; 2-methylanthracene; o-methylanthracene; 9,10-dimethylphenanthrene; and 3-methyl-phenanthrene. Higher molecular weight alkylaromatic hydrocarbons can also be used as starting materials and include aromatic hydrocarbons such as are produced by the alkylation of aromatic hydrocarbons with olefin polymers. Such products are frequently referred to in the art as alkylate, and include hexylbenzene, nonylbenzene, dodecylbenzene, pentadecylbenzene, hexyltoluene, nonyltoluene, dodecyltoluene, pentadecytoluene, etc. Very often alkylate is obtained as a high boiling fraction in which the alkyl group attached to the aromatic nucleus varies in size from about $C_6$ to about $C_{12}$.

Generally, the hydroxy substituted aromatic compounds are the hydroxybenzenes, hydroxynaphthalenes, and bis-phenols. Useful hydroxy substituted aromatic compounds include phenol, o-cresol, m-cresol, p-cresol, catechol, resorcinol, hydroquinone, pyrogallol, alpha-naphthol, alphaanthrol, and methylaniline and bisphenol-A.

Suitable aromatic compounds substituted with halide groups include chlorobenzene, o-dichlorobenzene, p-dichlorobenzene, bromobenzene, o-dibromobenzene, and p-dibromobenzene.

Suitable aromatic compounds substituted with aryl or alkaryl groups include diphenyl, triphenyl, diphenylmethane, triphenylmethane, dinaphthyl, and stilbene.

Suitable alkoxy or aryloxy group substituted compounds include anisole and phenetole.

Suitable cycloalkyl group substituted compounds include phenylcyclohexane.

Suitable compounds substituted with at least two different types of groups include o-, m-, and p-chlorophenol, 2,5-dichlorophenol, thymol, m-ethylphenol, p-t-butylphenol, o-phenylphenol, p-phenylphenol, guaiacol, eugenol and isoeugenol.

Other aromatic methylatable compounds suitable in the process of this invention include phenyl acetate, indene and flourene.

Some suitable aromatic compounds possessing hetero atoms include thiophene, furan, and quinoline.

The alkylating agent which is used in the process of this invention is a mixture of hydrogen and/or a hydrogen-containing substance which provides hydrogen under process conditions and a carbon oxide, i.e., carbon monoxide and/or carbon dioxide. Gaseous mixtures of hydrogen and carbon monoxide, hydrogen and carbon dioxide, and hydrogen, carbon monoxide and carbon dioxide, which are obtained principally from the gasification of a fossil fuel such as coal or natural gas and when derived in this manner, are collectively referred to as synthesis gas or "syngas", are preferred alkylating agents herein.

A typical purified synthesis gas will have the composition, on a water-free basis, in volume percentages, as follows: hydrogen, 51; carbon monoxide, 40; carbon dioxide, 4; methane, 1; and nitrogen, 4.

The synthesis gas may be prepared from fossil fuels by any of the known methods, including such in situ gasification processes as the underground partial combustion of coal and petroleum deposits. The term fossil fuels, as used herein, is intended to include anthracite and bituminous coal, lignite, crude petroleum, shale oil, oil from tar sands, natural gas, as well as fuels derived from simple physical separations or more profound transformations of these materials, including coked coal, petroleum coke, gas oil, residua from petroleum distillation, and two or more of any of the foregoing materials in combination. Other carbonaceous fuels such as peat, wood and cellulosic waste materials also may be used.

Although various processes may be employed for the gasification, those of major importance depend either on the partial combustion of the fuel with an oxygen-containing gas or on the high temperature reaction of the fuel with steam, or on a combination of these two reactions.

The raw synthesis gas produced from fossil fuels will contain various impurities such as particulates, sulfur compounds, and metal carbonyl compounds, and will be characterized by a hydrogen-to-carbon oxides ratio which will depend on the fossil fuel and the particular gasification technology utilized. In general, it is desirable for the efficiency of subsequent conversion steps to purify the raw synthesis gas by the removal of impurities. Techniques for such purification are known and are not part of this invention.

Mixtures of carbon monoxide and a hydrogen-containing substance such as water which react under the conditions of the alkylation reaction to provide hydrogen can also be used.

The volume ratio of hydrogen to carbon oxide in the alkylating agent is not critical and can vary widely. In general, it is preferred to adjust the hydrogen-to-carbon monoxide volume ratio to be within the range of from 0.2 to 10 and particularly in the range of from 0.4 to 3 upon contact with the catalyst. Should the alkylating agent as prepared be excessively rich in carbon oxides, it may be brought within the preferred range by the well known water-gas shift reaction. Purified synthesis gas adjusted to containing the desired volume ratio of hydrogen-to-carbon monoxide or provided within the range of from 0.2 to 10 will be referred to as adjusted synthesis gas.

The heterogeneous catalyst of this invention comprises a metal or metal-containing component selected from the group consisting of iron, cobalt, ruthenium, manganese, rhodium and osmium, and a zeolite having a constraint index of 12 or less. Iron, cobalt and ruthenium are preferred herein, iron and cobalt for their relatively low cost and ruthenium, while expensive, for comparatively high level of activity.

The weight ratio of metal, calculated upon the basis of the metal in its free, i.e., uncombined, state to zeolite can range from about 0.1 to about 10 and preferably from about 0.3 to 3. In the case of the more active metals such as ruthenium, these ratios can vary from about 0.001 to about 1 and preferably from about 0.003 to 0.1.

The finished catalyst can be in the form of a loose mixture, pellet or an extrudate.

The metal or metal-containing component can be incorporated by a variety of methods. For example:

(1) The metal or metal containing component, preferably the oxide, is simply mixed or ground together with the zeolite.

(2) The metal in the form of a compound dissolved in a suitable solvent is impregnated onto an inert support such as activated carbon, silica, alumina, titania, magnesia, zirconia, clays, and the like, and following calcination to the oxide, the supported metal oxide is mixed with the zeolite.

(3) A solution of a compound of the metal as in method (2) is impregnated directly onto the zeolite followed by calcination of the compound to the oxide.

(4) The metal or metal-containing component is incorporated onto the zeolite during the crystallization step of manufacturing the zeolite.

(5) The metal or metal-containing component is incorporated onto the zeolite by ion exchange process.

(6) The metal or metal-containing component present as an intercalate in graphite is mixed with the zeolite.

When a metal compound other than an oxide is used, the compound can be converted to the oxide by any of the prior and conventional techniques of thermal decomposition (calcination) whose operational parameters are well known and do not constitute a part of this invention per se.

For impregnation employed in methods (2) and (3), metal salts and other compounds such as the metals in the form of their halides, nitrates, oxalates, carbonates, acetates, acetylacetonates, and the like, can be used. Aqueous or non-aqueous solvents, e.g., methanol, acetone, chloroform, hexane and benzene, can be used depending on the solubility of the metal compound selected.

After impregnation, the catalyst is vacuum dried at about 100° C. and then reduced at a temperature ranging from about 150° C. to about 600° C., and preferably from about 250° to about 500° C., with a reducing gas such as hydrogen or hydrogen containing gas such as $H_2/CO$ mixture to activate the catalyst. Activation can be carried out under pressure. However, in case $H_2/CO$ mixture is used, low pressure such as 1 atm. is preferred. The optimum time and temperature to accomplish activation depends on the particular compound used and can be determined experimentally for a given metal compound employing routine experimentation. It is, of course, within the scope of the present invention to effect activation in situ in the alkylation zone.

The foregoing catalysts can also be combined with one or more promoters, this being especially desirable when iron and/or cobalt are present. Suitable promoters include such metal and metal-containing components as the alkali metals, particularly potassium, the alkaline earth metals, and copper, the compounds of these metals, particularly the carbonates, and their mixtures. Typically, the promoters are added in fairly small quantities, e.g., up to 5% by weight of the metal component of the non-promoted catalyst.

The term "zeolite" herein defines a natural or synthetic porous tectosilicate characterized by having a rigid crystalline framework structure composed of an assembly of silicon atoms and at least a trace amount of a trivalent metal atom, preferably aluminum, but which can also be iron, boron, gallium, chromium, etc., or mixtures thereof, the silicon atoms and trivalent metal atoms each being surrounded by a tetrahedron of shared oxygen atoms, and a precisely defined pore structure. Exchangeable cations are present in the pores.

The preferred zeolites are selected from the natural and synthetic crystalline aluminosilicates. These zeolites induce profound transformations of aliphatic hydrocarbons to aromatic hydrocarbons in commercially desirable yields and are generally highly effective in alkylation, isomerization, disproportionation and other reactions involving aromatic hydrocarbons. Although they have unusually low alumina contents, i.e., high silica to alumina ratios, they are very active even with silica to alumina ratios exceeding 30 and exhibit activity even with very high silica to alumina ratios, e.g., 10,000 and even higher. This activity is surprising since catalytic activity of zeolites is generally attributed to framework aluminum atoms and cations associated with these aluminum atoms. These zeolites retain their crystallinity for long periods in spite of the presence of steam even at high temperatures which induce irreversible collapse of the crystal framework of other zeolites, e.g., of the X and A type. Furthermore, carbonaceous deposits, when formed, may be removed by burning at higher than usual temperatures to restore activity. In many environments the zeolites of this class exhibit very low coke forming capability, conducive to very long times on stream between burning regenerations.

An important characteristic of the crystal structure of this class of zeolites is that it provides constrained access to, and egress from, the intra-crystalline free space by virtue of having a pore dimension greater than about 5 Angstroms and pore windows of about a size such as would be provided by 10-membered rings of oxygen atoms. It is to be understood, of course, that these rings are those formed by the regular disposition of the tetrahedra making up the anionic framework of the crystalline aluminosilicate, the oxygen atoms themselves being bonded to the silicon or aluminum atoms at the centers of the tetrahedra. Briefly, the preferred zeolites useful in this invention possess, in combination: a silica to alumina ratio of at least about 12; and a structure providing constrained access to the crystalline free space.

The silica to alumina ratio referred to may be determined by conventional analysis. This ratio is meant to represent, as closely as possible, the ratio in the rigid anionic framework of the zeolite crystal and to exclude aluminum in the binder or in cationic or other form within the channels. Although zeolites with a silica to alumina ratio of at least 12 are useful, it is preferred to use zeolites having higher ratios of at least about 30. Such zeolites, after activation, acquire an intracrystalline sorption capacity for normal hexane which is greater than that for water, i.e., they exhibit "hydrophobic" properties. It is believed that this hydrophobic character is advantageous in the present invention.

The zeolites useful as catalysts in this invention freely sorb normal hexane and have a pore dimension greater than about 5 Angstroms. In addition, their structure must provide constrained access to some larger molecules. It is sometimes possible to judge from a known crystal structure whether such constrained access exists. For example, if the only pore windows in a crystal are formed by 8-membered rings of oxygen atoms, then access by molecules of larger cross-section than normal hexane is substantially excluded and the zeolite is not of the desired type. Zeolites with windows of 10-membered rings are preferred, although excessive puckering or pore blockage may render these zeolites substantially ineffective.

Rather than attempt to judge from crystal structure whether or not a zeolite possesses the necessary constrained access, a simple determination of the "constraint index" may be made by continuously passing a mixture of equal weight of normal hexane and 3-methylpentane over a small sample, approximately 1 gram or less, of zeolite at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 1,000° F. for at least 15 minutes. The zeolite is then flushed with helium and the temperature adjusted between 550° F. and 950° F. to give an overall conversion between 10% and 60%. The mixture of hydrocarbons is passed at 1 liqid hourly space velocity (i.e., 1 volume of liquid hydrocarbon per volume of catalyst per hour) over the zeolite with a helium dilution to give a helium to total hydrocarbon mole ratio of 4:1. After 20 minutes on stream, a sample of the effluent is taken and analyzed, most conveniently by gas chromatography, to determine the fraction remaining unchanged for each of the two hydrocarbons.

The "constraint index" is calculated as follows:

$$\text{Constraint Index} = \frac{\log_{10}(\text{fraction of n-hexane remaining})}{\log_{10}(\text{fraction of 3-methylpentane remaining})}$$

The constraint index approximates the ratio of the cracking rate constants for the two hydrocarbons. Catalysts suitable for the present invention are those which employ a zeolite having a constraint index of 12.0 or less. Constraint Index (CI) values for some typical zeolites included within the scope of this invention are:

| CAS | C.I. |
| --- | --- |
| ZSM-5 | 8.3 |
| ZSM-11 | 8.7 |
| ZSM-35 | 6.0 |
| TMA Offretite | 3.7 |
| ZSM-38 | 2.0 |
| ZSM-12 | 2 |
| Beta | 0.6 |
| ZSM-4 | 0.5 |
| Acid Mordenite | 0.5 |
| REY | 0.4 |

Zeolites with a constraint Index greater than 12 such as erionite (CI=38) are not useful for the purpose of this invention. In the practice of the present invention, zeolites having Constraint Index values above about 2 up to the maximum value of 12 are preferred for the production of alkylated aromatics in which the alkyl side changes are of relatively short length, e.g., from 2 to about 8 carbon atoms, and zeolites having Constraint Index values of 2 and less are preferred for the production of alkylated aromatics possessing relatively long side chains, e.g., from about 9 to about 22 carbon atoms. Thus, for example, zeolites such a those of the ZSM-5, ZSM-11 and ZSM-35 type are preferred for making short alkyl chain aromatics and those of the ZSM-4, ZSM-12 and ZSM-38 type are preferred for making long alkyl chain aromatics.

The above-described Constraint Index is an important, and even critical, definition of those zeolites which are useful to catalyze the instant process. The very nature of this parameter and the recited technique by which it is determined, however, admit of the possibility that a given zeolite can be tested under somewhat different conditions and thereby have different constraint indexes. Constraint Index seems to vary somewhat with severity of operation (conversion). Therefore, it will be appreciated that it may be possible to so select test conditions to establish multiple constraint indexes for a particular given zeolite which may be both inside and outside the above defined range of 12 and less.

Thus, it should be understood that the parameter and property "Constraint Index" as such value is used herein is an inclusive rather than an exclusive value. That is, a zeolite when tested by any combination of conditions within the testing definition set forth herein above to have a constraint index of 12 and less is intended to be included in the instant catalyst definition regardless that the same identical zeolite tested under other defined conditions may give a constraint index value above 12.

The class of preferred zeolites herein is exemplified by ZSM-5, ZSM-11, ZSM-12, ZSM-21, and other similar materials. U.S. Pat. No. 3,702,886 describing and claiming ZSM-5 is incorporated herein by reference.

ZSM-11 is more particularly described in U.S. Pat. No. 3,709,979, the entire contents of which are incorporated herein by reference.

ZSM-12 is more particularly described in U.S. Pat. No. 3,832,449, the entire contents of which are incorporated herein by reference.

Evidence has been adduced which suggests that ZSM-21 may be composed of at least two (2) different zeolites designated ZSM-35 and ZSM-38, one or both of which are the effective material insofar as the catalysis of this invention is concerned. ZSM-35 is described in U.S. Pat. Nos. 4,016,245 and ZSM-38 is described in 4,046,859.

The specific zeolites described, when prepared in the presence of organic cations, are substantially catalytically inactive, possibly because the intracrystalline free space is occupied by organic cations from the forming solution. They may be activated by heating in an inert atmosphere at 1000° F. for one hour, for example, followed by base exchange with ammonium salts followed by calcination at 1000° F. in air. The presence of organic cations in the forming solution may not be absolutely essential to the formation of this special type of zeolite. More generally, it is desirable to activate this type zeolite by base exchange with ammonium salts followed by calcination in air at about 1000° F. for from about 15 minutes to about 24 hours.

Natural zeolites may sometimes by converted to this type zeolite by various activation procedures and other treatments such as base exchange, steaming, alumina extraction and calcination, alone or in combination. Natural minerals which may be so treated include ferrierite, brewsterite, stilbite, dachiardite, epistilbite, heulandite and clinoptilolite. The preferred crystalline aluminosilicates are ZSM-5, ZSM-11, ZSM-12 and ZSM-21, with ZSM-5 particularly preferred.

The zeolites used as catalysts in this invention may be in the hydrogen form or they may be base exchanged or impregnated to contain ammonium or a metal cation complement. It is desirable to calcine the zeolite after base exchange. The metal cations that may be present include any of the cations of the metals of Groups I through VIII of the periodic table. However, in the case of Group IA metals, the cation content should in no case be so large as to substantially eliminate the activity of the zeolite for the catalysis being employed in the instant invention.

In a preferred aspect of this invention, the zeolites useful as catalysts herein are selected as those having a crystal framework density, in the dry hydrogen form, of not substantially below about 1.6 grams per cubic centimeter. It has been found that zeolites which satisfy all three of these criteria are most desired. Therefore, the preferred catalysts of this invention are those comprising zeolite having a constraint index as defined above of about 12 or less, a silica to alumina ratio of at least about 12 and a dried crystal density of not substantially less than about 1.6 grams per cubic centimeter. The dry density for known structures may be calculated from the number of silicon plus aluminum atoms per 1000 cubic Angstroms, as given, e.g., on page 19 of the article on Zeolite Structure by W. M. Meier. This paper, the entire contents of which are incorporated herein by reference, is included in "Proceedings of the Conference on Molecular Sieves, London, April 1967", published by the Society of Chemical Industry, London, 1968. When the crystal structure is unknown, the crystal framework density may be determined by classical pyknometer techniques. For example, it may be determined by immersing the dry hydrogen form of the zeolite in an organic solvent which is not sorbed by the crystal. It is possible that the unusual sustained activity and stability of this class of zeolites is associated with a relatively small amount of free space within the crystal, which might be expected to result in more stable structures. This free space, however, seems to be important as the locus of catalytic activity.

Crystal framework densities of some typical useful zeolites are:

| Zeolite | Void Volume | Framework Density |
|---|---|---|
| Ferrierite | 0.28 cc/cc | 1.76 g/cc |
| Mordenite | .28 | 1.7 |
| ZSM-5, -11 | .29 | 1.79 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Gmelinite | .44 | 1.46 |
| Chabazite | .47 | 1.45 |
| A | .5 | 1.3 |
| Y | .48 | 1.27 |

In the process of this invention, the starting aromatic compound(s) and the alkylating agent are contacted with the catalyst in an alkylation zone maintained at elevated temperature, e.g., from about 180° C. to about 450° C. and preferably from about 210° C. to about 400° C. Pressure within the alkylation zone can vary widely and pressures on the order of from atmospheric to about 100 atmospheres, advantageously from about 6 to about 60 atmospheres generally provide good results. The amount of catalyst required can also vary and for practical rates of conversion, will ordinarily be sufficient to provide a gas hourly space velocity, (GHSV) at standard temperature and pressure (STP) of from about 30 to about 10,000 and preferably from about 100 to about 3,000. It is preferred to use a stoichiometric excess of aromatic compound(s) compared to the carbon oxide(s) content of the alkylating agent in order to insure maximum consumption of the latter. Suitable mole ratios of aromatic compound(s) to carbon oxide(s) range from about 0.1 to about 20 and preferably from about 0.2 to about 5.

The heterogeneous catalyst can be contained as a fixed bed, a fluidized bed or a liquid slurry reactor may be used. The product stream containing the alkyl aromatic mixture, unreacted gases and steam can be cooled and the hydrocarbons recovered by any of the techniques known in the art, which techniques do not constitute part of this invention. The recovered alkyl aromatics can be further separated by distillation or other means to provide relatively pure alkyl aromatics.

The following example is further illustrative of the process of the present invention:

EXAMPLE

A reactor in which alkylation was carried out was operated under the conditions and with the results indicated below.

| ALKYLAROMATICS FROM REACTION OF BENZENE WITH SYNGAS | |
|---|---|
| Temperature, °C. | 315 |
| Pressure, atmospheres | 25 |
| Catalyst | Co-precipitated Fe—K—Cu*/HZSM-5 |
| Volume ratio of hydrogen to carbon monoxide | 0.68 |
| Mole ratio of benzene to carbon monoxide | 0.6 |
| GHSV | 630 |
| Total syngas conversion, mole % | 97 |
| Trapping efficiency**, % | 58 |
| Alkylaromatics distribution wt. % | |
| Ethylbenzene | 6 |
| Propylbenzenes | 47 |
| Butylbenzenes | 25 |
| Pentylbenzenes | 12 |
| Hexylbenzene | 5 |
| Other (methyl aromatics) | 5 |
| | 100 |

*Fe 65%; K 0.31%; Cu 0.31%.
**Defined as the percentage of hydrocarbons which are produced from syngas but are subsequently converted to the alkyl groups of alkylaromatics by reacting with benzene.

As described above, the alkylaromatic product stream resulting from the process of the present invention, with or without being separated into its individual components or a plurality of fractions, can be subjected to dealkylation in accordance with known and conventional procedures, themselves not constituting a part of this invention per se, to provide olefin. The dealkylated aromatic can thereafter be recycled to the alkylation zone to trap additional quantities of hydrocarbons in the form of alkyl groups. In general, dealkylation is carried out employing acidic catalysts such as silica, silica-alumina, magnesia, zeolites, etc., at a temperature of from about 400° C. to about 650° C., preferably from about 450° C. to about 600° C., and a pressure of from about 1 atmosphere to about 20 atmospheres, preferably from about 2 atmospheres to about 10 atmospheres. Hydrogen is preferably present in the dealkylation zone in order to increase catalyst stability.

What is claimed is:

1. A process for alkylating an aromatic compound to provide a product aromatic compound possessing at least one more alkyl group of at least two carbon atoms than the starting aromatic compound, which comprises reacting at elevated temperature at least one aromatic compound possessing at least one hydrogen atom directly bonded to the aromatic nucleus with an alkylating agent which is a mixture of hydrogen and/or a hydrogen-containing substance which provides hydrogen under process conditions and a carbon oxide, in the presence of a catalyst comprising a metal or metal-containing component, selected from the group consisting of iron, cobalt, ruthenium, manganese, rhodium and osmium, and a zeolite having a constraint index of 12 or less whereby said product aromatic compound is produced.

2. The process of claim 1 wherein the starting aromatic compound is benzene.

3. The process of claim 1 wherein the metal or metal-containing component is iron, cobalt or ruthenium.

4. The process of claim 1 wherein the zeolite is ZSM-5.

5. The process of claim 1 wherein the alkylating agent is a gaseous mixture of hydrogen and carbon monoxide.

6. The process of claim 1 wherein the product aromatic compound is subjected to dealkylation to provide olefin and the starting aromatic compound, the latter being separated from the olefin and recycled to the alkylation reaction.

* * * * *